US008936778B2

(12) United States Patent
Fischer

(10) Patent No.: US 8,936,778 B2
(45) Date of Patent: *Jan. 20, 2015

(54) METHODS FOR BLEACHING AND DESENSITIZING TEETH

(75) Inventor: Dan E. Fischer, Sandy, UT (US)

(73) Assignee: Ultradent Products, Inc., South Jordan, UT (US)

(*) Notice: Subject to any disclaimer, the term of this patent is extended or adjusted under 35 U.S.C. 154(b) by 1258 days.

This patent is subject to a terminal disclaimer.

(21) Appl. No.: 11/733,490

(22) Filed: Apr. 10, 2007

(65) Prior Publication Data

US 2007/0196287 A1 Aug. 23, 2007

Related U.S. Application Data

(63) Continuation of application No. 09/710,181, filed on Nov. 10, 2000, which is a continuation-in-part of application No. 09/494,113, filed on Jan. 13, 2000, now abandoned, and a continuation-in-part of application No. 09/694,516, filed on Oct. 23, 2000, now Pat. No. 6,368,576, and a continuation-in-part of application No. 09/190,709, filed on Nov. 12, 1998, now Pat. No. 6,309,625.

(51) Int. Cl.
| *A61Q 11/00* | (2006.01) |
| *A61K 8/22* | (2006.01) |
| *A61K 8/21* | (2006.01) |
| *A61K 8/19* | (2006.01) |
| *A61K 8/24* | (2006.01) |
| *A61K 8/38* | (2006.01) |

(52) U.S. Cl.
CPC . *A61Q 11/00* (2013.01); *A61K 8/19* (2013.01); *A61K 8/21* (2013.01); *A61K 8/22* (2013.01); *A61K 8/24* (2013.01); *A61K 8/38* (2013.01); Y10S 514/944 (2013.01)
USPC ............. 424/53; 424/49; 424/52; 424/401; 424/673; 433/215; 433/216; 433/217.1; 514/944

(58) Field of Classification Search
CPC ..... A61Q 11/00; A61Q 17/0053; A61K 8/22; A61K 6/0017; A61K 8/21; A61K 33/40; A61K 9/006; A61C 19/063; A61C 19/066; Y10S 514/944
USPC ........ 424/49, 52, 53, 401, 673; 433/215, 216, 433/217.1; 514/944
See application file for complete search history.

(56) References Cited

U.S. PATENT DOCUMENTS

| 1,371,029 A | 3/1921 | Jennings |
| 1,642,653 A | 9/1927 | Goldstein |
| 1,691,785 A | 11/1928 | Remensnyder |
| 1,818,146 A | 8/1931 | Maker |
| 1,934,688 A | 11/1933 | Ackerman |
| 2,257,709 A | 9/1941 | Anderson |
| 2,798,053 A | 7/1957 | Brown |
| 2,835,628 A | 5/1958 | Saffir .............................. 167/84 |
| 2,858,281 A | 10/1958 | Bauman et al. |
| 2,923,692 A | 2/1960 | Ackerman et al. |
| 2,985,625 A | 5/1961 | Jones |
| 3,060,935 A | 10/1962 | Riddell |
| 3,073,300 A | 1/1963 | Berghash |
| 3,107,668 A | 10/1963 | Thompson |
| 2,669,988 A | 2/1965 | Carpenter |
| 3,224,441 A | 12/1965 | Monaghan |
| 3,224,443 A | 12/1965 | Monaghan |
| 3,234,942 A | 2/1966 | Simor |
| 3,247,844 A | 4/1966 | Berghash |
| 3,250,272 A | 5/1966 | Greenberg |
| 3,319,626 A | 5/1967 | Lindsay |
| 3,339,547 A | 9/1967 | Drabkowski .................. 128/260 |
| 3,379,193 A | 4/1968 | Monaghan .................... 128/136 |
| 3,380,446 A | 4/1968 | Martin ............................ 128/24 |
| 3,385,291 A | 5/1968 | Martin |

(Continued)

FOREIGN PATENT DOCUMENTS

| DE | 1 489 712 | 11/1965 |
| DE | 1566227 | 10/1969 |

(Continued)

OTHER PUBLICATIONS

Den-Mat Corporation advertisement for "Rembrandt Xtra-Comfort Bleaching Gel" in Dental Products Report, p. 2 (Nov. 1998).
File History of U.S. Patent No. 7,125,543 to Hodosh (U.S. Appl. No. 11/230,404, filed Sep. 20, 2005).
File History of U.S. Appl. No. 09/072,504, filed May 4, 1998, now abandoned.
Haywood, V., "Effectiveness, Side Effects and Long-Term Status of Nightguard Vital Bleaching", J. Am. Dent. Assn., vol. 125, pp. 1219-1226 (Sep. 1994).

(Continued)

*Primary Examiner* — Lezah Roberts
(74) *Attorney, Agent, or Firm* — Workman Nydegger

(57) ABSTRACT

Composition and methods include a dental bleaching agent, potassium nitrate a fluoride salt for enhanced whitening and reduced tooth sensitivity. The potassium nitrate and fluoride salt both reduce or eliminate tooth sensitivity that may otherwise be caused by the bleaching agent. For prolonged treatment of teeth, lower quantities of potassium nitrate (e.g., 0.5%) have actually been found to work better than larger quantities (e.g., 3%). The dental compositions may be applied directly to the person's teeth, or they may be loaded into a comfortable fitting, flexible, thin-walled dental tray and placed over the person's teeth. In that case, the dental compositions will include a tackifying agent, such as carboxypolymethylene, which assists the composition in retaining the dental tray over the person's teeth as a result of the adhesive properties of the dental composition rather than due to mechanical interlocking of the tray over the person's teeth. The dental compositions may further include anticariogenic and antimicrobial agents.

21 Claims, 5 Drawing Sheets

(56) References Cited

U.S. PATENT DOCUMENTS

| | | | |
|---|---|---|---|
| 3,399,457 A | 9/1968 | Hagman | |
| 3,416,527 A | 12/1968 | Hoef | 128/260 |
| 3,448,738 A | 6/1969 | Berghash | |
| 3,481,329 A | 12/1969 | Warren, Jr. | |
| 3,499,844 A | 3/1970 | Kibbel et al. | |
| 3,505,995 A | 4/1970 | Greenberg | |
| 3,527,218 A | 9/1970 | Westine | |
| 3,527,219 A | 9/1970 | Greenberg | 128/260 |
| 3,536,069 A | 10/1970 | Gores | 128/136 |
| 3,567,823 A | 3/1971 | Yamaga et al. | 424/132 |
| 3,624,909 A | 12/1971 | Greenberg | |
| 3,625,215 A | 12/1971 | Quisling | 128/260 |
| 3,657,413 A | 4/1972 | Rosenthal | |
| 3,688,406 A | 9/1972 | Porter et al. | 32/40 |
| 3,742,942 A | 7/1973 | Westline | |
| 3,844,286 A | 10/1974 | Cowen | 128/260 |
| 3,863,006 A | 1/1975 | Hodosh | |
| 165,584 | 7/1975 | Hopfen | |
| 3,911,104 A | 10/1975 | Harrison | 424/52 |
| 3,955,281 A | 5/1976 | Weitzman | 32/14 |
| 3,969,499 A | 7/1976 | Lee, Jr. et al. | 424/52 |
| 3,976,223 A | 8/1976 | Jass et al. | |
| 3,988,433 A | 10/1976 | Benedict | 424/53 |
| 3,998,945 A | 12/1976 | Vit | |
| 4,012,839 A | 3/1977 | Hill | |
| 4,032,627 A | 6/1977 | Suchan et al. | |
| 4,044,762 A | 8/1977 | Jacobs | 128/136 |
| 4,057,621 A | 11/1977 | Pashley et al. | |
| 4,064,628 A | 12/1977 | Weitzman | 33/14 |
| 4,138,814 A | 2/1979 | Weitzman | |
| 4,164,940 A | 8/1979 | Quinby | |
| 4,173,219 A | 11/1979 | Lentine | 128/260 |
| 4,173,505 A | 11/1979 | Jacobs | 156/285 |
| 4,239,818 A | 12/1980 | LaBate | |
| 4,244,942 A | 1/1981 | Kamishita et al. | |
| 4,251,507 A | 2/1981 | Olson | 424/49 |
| 4,283,385 A | 8/1981 | Dhabhar et al. | 424/52 |
| 4,302,441 A | 11/1981 | Muhlemann et al. | |
| 4,343,608 A | 8/1982 | Hodosh | |
| 4,357,318 A | 11/1982 | Shah et al. | 424/52 |
| 4,376,628 A | 3/1983 | Aardse | |
| 4,400,373 A | 8/1983 | Hodosh | |
| 4,407,675 A | 10/1983 | Hodosh | |
| 4,419,992 A | 12/1983 | Chorbajian | |
| 4,428,373 A | 1/1984 | Seid et al. | 604/77 |
| 4,431,631 A | 2/1984 | Clipper et al. | 424/53 |
| 4,518,721 A | 5/1985 | Dhabhar et al. | |
| 4,522,805 A | 6/1985 | Gordon | 424/52 |
| 4,522,806 A | 6/1985 | Muhlemann et al. | |
| 4,528,180 A | 7/1985 | Schaeffer | 424/52 |
| 4,537,778 A | 8/1985 | Clipper et al. | 424/53 |
| 4,544,354 A | 10/1985 | Gores et al. | 433/42 |
| 4,557,692 A | 12/1985 | Chorbajian | |
| 4,560,351 A | 12/1985 | Osborne | 433/80 |
| 4,568,536 A | 2/1986 | Kronenthal et al. | |
| 4,592,487 A | 6/1986 | Simon et al. | 222/94 |
| 4,592,488 A | 6/1986 | Simon et al. | 222/94 |
| 4,631,185 A | 12/1986 | Kim | |
| 4,645,662 A | 2/1987 | Nakashima et al. | 424/52 |
| 4,661,070 A | 4/1987 | Friedman | 433/203.1 |
| 4,687,663 A | 8/1987 | Schaeffer | 424/52 |
| 4,696,757 A | 9/1987 | Blank et al. | |
| 4,751,072 A | 6/1988 | Kim | |
| 4,755,386 A | 7/1988 | Hsiao et al. | |
| 4,770,634 A | 9/1988 | Pellico | 433/217 |
| 4,788,052 A | 11/1988 | Ng et al. | |
| 4,812,308 A | 3/1989 | Winston et al. | 424/52 |
| 4,839,156 A | 6/1989 | Ng et al. | |
| 4,839,157 A | 6/1989 | Mei-King Ng et al. | |
| 4,849,213 A | 7/1989 | Schaeffer | 424/53 |
| 4,895,721 A | 1/1990 | Drucker | |
| 4,902,227 A | 2/1990 | Smith | 433/215 |
| 4,939,284 A | 7/1990 | Degenhardt | 558/142 |
| 4,954,487 A | 9/1990 | Cooper et al. | |
| 4,966,777 A | 10/1990 | Gaffab et al. | 424/52 |
| 4,968,251 A | 11/1990 | Darnell | 433/216 |
| 4,971,782 A | 11/1990 | Rudy et al. | |
| 4,980,152 A | 12/1990 | Frazier et al. | 424/52 |
| 4,983,379 A | 1/1991 | Schaeffer | 424/52 |
| 4,983,380 A * | 1/1991 | Yarborough | 433/215 |
| 4,983,381 A | 1/1991 | Torres Zaragoza | |
| 4,988,500 A | 1/1991 | Hunter et al. | 424/53 |
| 4,990,089 A | 2/1991 | Munro | 433/215 |
| 4,992,258 A | 2/1991 | Mason | 424/49 |
| 5,015,466 A | 5/1991 | Parran, Jr. et al. | 424/52 |
| 5,098,303 A | 3/1992 | Fischer | 433/215 |
| 5,122,365 A | 6/1992 | Murayama | |
| 5,153,006 A | 10/1992 | Hodosh | |
| 5,182,099 A | 1/1993 | Jönsson et al. | 424/49 |
| 5,188,822 A | 2/1993 | Viccaro et al. | 424/52 |
| RE34,196 E | 3/1993 | Munro | |
| 5,234,342 A | 8/1993 | Fischer | 433/215 |
| 5,240,697 A | 8/1993 | Norfleet et al. | 424/52 |
| 5,256,402 A | 10/1993 | Prencipe et al. | 424/53 |
| 5,352,439 A | 10/1994 | Norfleet et al. | 424/52 |
| 5,374,417 A | 12/1994 | Norfleet et al. | 424/49 |
| 5,376,006 A | 12/1994 | Fischer | 433/215 |
| 5,401,495 A | 3/1995 | Murayama | |
| 5,403,577 A | 4/1995 | Friedman | 424/45 |
| 5,409,631 A | 4/1995 | Fischer | 252/186.26 |
| 5,427,768 A | 6/1995 | Tung | 424/52 |
| 5,437,858 A | 8/1995 | Hungerbach et al. | |
| 5,449,509 A | 9/1995 | Jackson et al. | 424/49 |
| 5,505,933 A | 4/1996 | Norfleet et al. | 424/52 |
| 5,522,726 A | 6/1996 | Hodosh | 433/215 |
| 5,565,190 A | 10/1996 | Santalucia et al. | |
| 5,571,501 A | 11/1996 | Toy | 424/49 |
| 5,599,527 A | 2/1997 | Hsu et al. | 424/52 |
| 5,614,174 A | 3/1997 | Hsu et al. | 424/49 |
| 5,626,837 A | 5/1997 | Shimada et al. | |
| 5,630,999 A | 5/1997 | Burke et al. | 424/49 |
| 5,631,000 A | 5/1997 | Pellico et al. | |
| 5,648,064 A | 7/1997 | Gaffar et al. | 424/53 |
| 5,698,182 A | 12/1997 | Prencipe et al. | 424/53 |
| 5,725,843 A | 3/1998 | Fischer | 424/49 |
| 5,827,505 A | 10/1998 | Hughes et al. | 424/49 |
| 5,851,512 A | 12/1998 | Fischer | 424/49 |
| 5,855,870 A | 1/1999 | Fischer | 424/49 |
| 5,985,249 A | 11/1999 | Fischer | 424/49 |
| 6,036,943 A | 3/2000 | Fischer | |
| 6,099,868 A | 8/2000 | Hodosh | |
| 6,108,850 A | 8/2000 | McLaughlin | 15/167.1 |
| 6,280,708 B1 | 8/2001 | Ryles et al. | 424/53 |
| 6,306,370 B1 | 10/2001 | Jensen et al. | 424/49 |
| 6,309,625 B1 | 10/2001 | Jensen et al. | 424/49 |
| 6,322,774 B1 | 11/2001 | Jensen et al. | 242/53 |
| 6,368,576 B1 | 4/2002 | Jensen et al. | 424/49 |
| 6,458,340 B1 | 10/2002 | Ibsen et al. | 424/53 |
| 767,553 A1 | 8/2004 | Edgelow | |
| 803,474 A1 | 10/2005 | Dennis | |
| 803,475 A1 | 10/2005 | Dennis | |
| 7,125,543 B2 | 10/2006 | Hodosh | 424/53 |
| 2002/0155070 A1 | 10/2002 | Chen | |

FOREIGN PATENT DOCUMENTS

| | | | |
|---|---|---|---|
| DE | 2848237 | 11/1978 | |
| EP | 0 286 766 | 10/1988 | |
| EP | 0 325 267 | 7/1989 | |
| ES | 528007 | 12/1983 | |
| JP | 08-175943 | 9/1996 | |
| NL | 8100383 | 8/1982 | |
| WO | WO98/55001 | 12/1998 | A46B 11/04 |
| WO | WO00/28953 | 5/2000 | A61K 7/16 |

OTHER PUBLICATIONS

Hodosh, M., "A superior desensitizer—potassium nitrate", J. Am. Dent. Assn., vol. 88, pp. 831-832 (Apr. 1974).

U.S. Appl. No. 60/048,423, filed Jun. 3, 1997.

Ekstrand, Jan et al., "Systemic Flruoride Absorption Following Fluoride Gel Application," J. Dent. Res., vol. 59, No. 6, p. 1067 (Jun. 1980).

(56) References Cited

OTHER PUBLICATIONS

Englander et al., "Clinical Anticaries Effect of Repeated Topical Sodium Fluoride Applications by Mouthpieces", *JADA*, vol. 75, pp. 638-644 (Sep. 1967).
Kirkegaard et al., "Children's Response to Various Local Fluoride Treatments", Acta Odontol. Scand., vol. 38, No. 4, pp. 235-240 (1980).
LeCompte, E.J. et al., "Oral Fluoride Retention Following Various Topical Application Techniques in Children," J. Dent. Res., vol. 61, No. 12, pp. 1397-1400 (1982).
Myers, Malcolm, et al., "Effect of Daily Application of Fluoride in a Custom Fitted Mouthpiece on Plaque Flora Associated with Dental Decay", Journal of Dental Research, vol. 50, No. 3, pp. 597-599 (May 1971).
Newbrun, E., "Topical Fluoride Therapy: Discussion of Some Aspects of Toxicology, Safety, and Efficacy," J. Dent. Res., vol. 66, No. 5, pp. 1084-1086 (1987).
Trask, P., "Orthodontic Positioner Used for Home Fluoride Treatments", American Journal of Orthodontics, vol. 67, No. 6, pp. 677-682 (Jun. 1975).
Den-Mat Corporation advertisement for "Rembrandt Xtra-Comfort Bleaching Gel" in Dental Products Report , p. 2 (Nov. 1998).
Bayless, J. Mark et al., "Diagnosis and Treatment of Acute Fluoride Toxicity," JADA, vol. 110, pp. 209-211, Feb. 1985.
Blaine, Edward et al., "Oral Hygiene Supplement for Handicapped Children," The Journal of Dental Practice, pp. 29-31, May 1971.
Bouschor, Charles F., "Bleaching Fluorosis Stained Teeth," New Mexico Dental Journal, vol. 16, No. 1, pp. 33-34, May 1965.
Colon, P.G. Jr., "Removing Fluorosis Stains From Teeth," Quintessence International, vol. 2, No. 6, p. 1.
Database WPI, Section Ch, Week 200055, Derwent Publications Ltd., London, GB; Clas D21, An 2000-527064 XP002278903 & ES 21 147 252 A (Farmaklinica Dental SL), Sep. 1, 2000 Abstract.
*Dental Products Report* Medical Dental Communications, p. 2, Nov. 1998.
Den-Mat Corporation advertisement for "Rembrandt Lighten Bleaching Gel," Dental Products Report, p. 97, Feb. 1990.
Dickstein, Benjamin, "Neonatal Oral Candidasis: Evaluation of a New Chemotherapeutic Agent," Clinical Pediatrics, pp. 485-488, Aug. 1964.
Dietz, Ellen Roberta, "Bleaching Vital Teeth," The Dental Assistant, pp. 7-8, Jan./Feb. 1988.
Englander, H.R. et al., "The Prevention of Dental Caries in the Syrian Hamster after Repeated Topical Application of Sodium Fluoride Gels," JADA, vol. 73, pp. 1342-1347, Dec. 1966.
Fasanaro, Tom S., Bleaching Teeth: History, Chemicals, and Methods Used for Common Tooth Discolorations, Second Edition, Jan. 1991.
Feiglin, Barry, "A 6-year Recall Study of Clinically Chemically Bleached Teeth," Oral Surg. Oral Med. Oral Panthol, vol. 63, pp. 610-613, May 1987.
Genesis 2000 Advertisement for "Genesis White" Whitening System, Mar. 21, 1990.
Hodosh, M., "Capping Carious Exposed Pulps With Potassium Nitrate, Dimethyl Isosorbide, Polycarboxylate Cement," Jan. 2003, www.dentistrytoday.net/ME2/dirmod.asp?sid=&nm=&type+Publishing&mod=Publications%3A%3AArticle&mid=8F3A7027421841978F18BE895F87F791&tier=4&id=DA6122BC3CD148A4A3D7D41796B601E6.
Horii, A.A. et al., "A Vinyl Applicator for Assessing Drugs in the Treatment of Caries and Peridontal Disease in the Hamster," Laboratory of Histology and Pathology, National Institute of Dental Reseach, National Institutes of Health, Department of Health, Education and Welfare, U.S Public Health Service, Bethesda Maryland, p. 152, Aug. 19, 1963.
Kundergren et al., "In Vivo and In Vitro Studies on a New Peroxide-Containing Toothpaste," Scand. J. Dent. Res., vol. 81, pp. 544-547, 1973.
M&M Innovations advertisement for "Nu-Smile" dental bleaching system originally appearing in Dental Products Report, Nov. 1989.
Murrin, James R. et al., "Effect of Daily Application of Fluoride in a Custom Fitted Mouthpiece on Plaque Flora Associated with Dental Decay," Journal of Dental Research, vol. 50, No. 3, pp. 597-599, May 1971.
Nathanson, Dan et al., "Bleaching Vital Teeth: A Review and Clinical Study," Compend Contin. Educ. Dent., vol. VIII, No. 7, pp. 490-498.
Nagata, T. "Clinical Evaluation of a Potassium Nitrate Dentifrice for the Treatment of Dentinal Hypersensitivity," J. Clin. Periodontol, vol. 21, pp. 217-221, 1994.
Omnii International advertisement for White & Brite, Mar. 21, 1990.
Omnii International advertisement for Fluorides, etc., Mar. 21, 1990.
Ripa, Louis W. et al., "Effect of Prior Toothcleaning on Biannual Professional APF Topical Fluoride Gel-tray Treatments," Clinical Preventative Dentistry, vol. 5, No. 4, Jul.-Aug. 1983.
Ripa, Louis W. et al., "Effect of Prior Toothcleaning on Biannual Professional Acidulated Phosphate Fluoride Topical Fluoride Gel-tray Treatments—Results After Three Years," Caries Res. 18: pp. 457-464, 1984.
Wayman, Blake E. et al.,"Vital Bleaching Technique for Treatment of Endemic Fluorosis," General Dentistry, pp. 424-427, Sep./Oct. 1981.
Weisz, W.S., "Reduction of Dental Caries Through the Use of a Sodium Fluoride Mouthwash," The Journal of the American Dental Association, vol. 60, pp. 454-455, Apr. 1960.
Office Action dated Feb. 18, 2010 cited in U.S. Appl. No. 09/710,181.
Office Action dated Sep. 18, 2009 cited in U.S. Appl. No. 09/710,181.
Office Action dated Mar. 2, 2009 cited in U.S. Appl. No. 09/710,181.
Office Action dated Sep. 15, 2008 cited in U.S. Appl. No. 09/710,181.
Office Action dated Apr. 16, 2008 cited in U.S. Appl. No. 09/710,181.
Office Action dated Aug. 23, 2005 cited in U.S. Appl. No. 09/710,181.
Office Action dated Apr. 5, 2005 cited in U.S. Appl. No. 09/710,181.
Office Action dated Aug. 25, 2004 cited in U.S. Appl. No. 09/710,181.
Office Action dated Mar. 31, 2004 cited in U.S. Appl. No. 09/710,181.
Office Action dated Aug. 8, 2003 cited in U.S. Appl. No. 09/710,181.
Office Action dated Oct. 1, 2002 cited in U.S. Appl. No. 09/710,181.
Office Action dated Jul. 28, 2010 cited in U.S. Appl. No. 09/710,181.

* cited by examiner

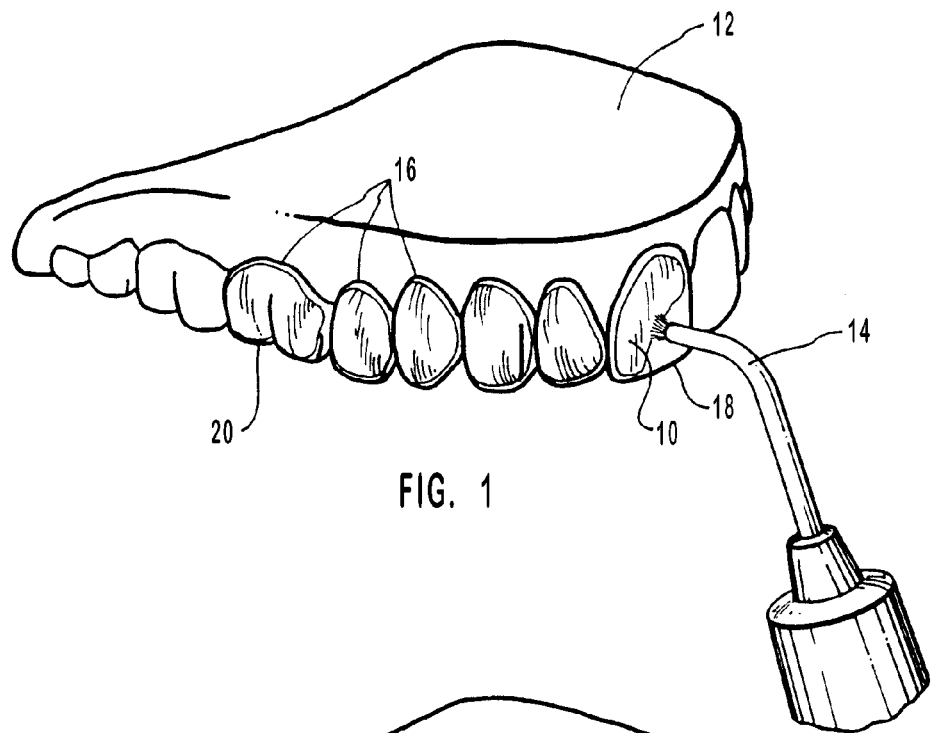
FIG. 1
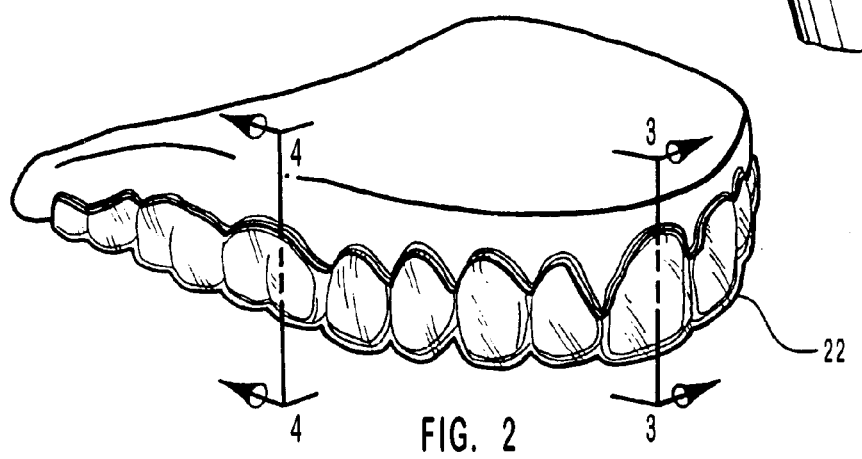
FIG. 2
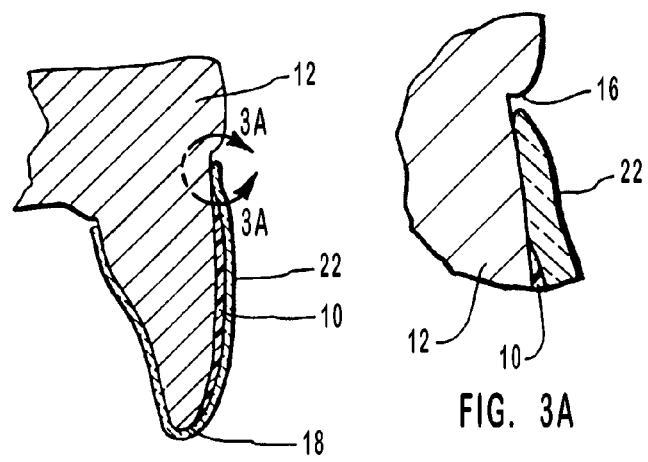
FIG. 3
FIG. 3A

METHODS FOR BLEACHING AND DESENSITIZING TEETH

CROSS-REFERENCE TO RELATED APPLICATIONS

This application is a continuation of co-pending U.S. application Ser. No. 09/710,181, filed Nov. 10, 2000, which is a continuation-in-part of U.S. application Ser. No. 09/494,113, filed Jan. 31, 2000, now abandoned, and also a continuation-in-part of U.S. application Ser. No. 09/694,516, filed Oct. 23, 2000, now U.S. Pat. No. 6,368,576, which is a continuation-in-part of U.S. application Ser. No. 09/190,709, filed Nov. 12, 1998, now U.S. Pat. No. 6,309,625. The disclosures of the foregoing applications and patents are incorporated herein in their entirety.

BACKGROUND OF THE INVENTION

1. The Field of the Invention

The present invention relates to compositions and methods for whitening and desensitizing teeth. More particularly, the present invention encompasses compositions that include both a bleaching agent and a desensitizing agent. Such compositions are especially suitable for maximized tooth whitening and minimized tooth sensitivity when in prolonged contact with the teeth to be treated.

2. The Relevant Technology

The natural color of teeth is opaque to translucent white or slightly off-white. However, the use of certain foods and tobacco, the process of aging, diseases, trauma, medications, some congenital conditions, and environmental effects can cause teeth to become discolored. Because whiter teeth are considered to be aesthetically superior to stained or discolored teeth, there has been a large demand for dental bleaching compositions.

Typical tooth bleaching agents release active oxygen radicals. Such bleaching agents include peroxides, such as hydrogen peroxide, percarbonates and perborates of the alkali and alkaline earth metals, or complex compounds containing hydrogen peroxide. Also, peroxide salts of the alkali or alkaline earth metals and peroxyacetic acid ($CH_3C=OO-OH$) are known to be useful in whitening teeth.

The most commonly used dental bleaching agent is carbamide peroxide ($CO(NH_2)_2 \cdot H_2O_2$), also called urea hydrogen peroxide, hydrogen peroxide carbamide, and perhydrol-urea. Carbamide peroxide has been used by dental clinicians for several decades as an oral antiseptic. Tooth bleaching was an observed side effect of extended contact time. Over-the-counter compositions of 10% carbamide peroxide are available as GLY-OXIDE® by Marion Laboratories and PROXI-GEL® by Reed and Carnrick. A sticky bleaching gel which is able to hold a comfortable-fitting dental tray in position for an extended time period is available under the trademark OPALESCENCE® from Ultradent Products, Inc. in South Jordan, Utah.

Patients who have desired to have their teeth whitened have typically done so by applying a bleaching composition to the teeth by means of a dental tray for repeated treatments, or they have had to submit to conventional in-office bleaching techniques that required from 4 to 10 visits to the dental office before clinically significant results were achieved. Clinically significant results are quantifiable such as by measuring gray scale, $L^*$, and as to yellowness or blueness, $b^*$, in the CIE® system of color measurement or by equivalent methods.

Although dental bleaching compositions are effective in removing stains and superficial discoloration, they are often limited by the inherent translucence of many people's teeth. More precisely, teeth having more translucent enamel are difficult to whiten beyond a certain point since the yellowish or grayish tint of the underlying dentin is difficult to change by bleaching alone.

Another downside of tooth bleaching regimens is the tendency of tooth bleaching agents to cause increased sensitivity when applied to teeth over prolonged periods of time. Thus, attempts to further whiten a person's teeth, including prolonged bleaching of excessively translucent teeth, may result in increased tooth sensitivity, which can become quite severe for some people.

From the foregoing, it will be appreciated that what is needed in the art are improved compositions and methods for whitening teeth.

It will also be appreciated that what is also needed are improved compositions and methods for whitening teeth which reduce tooth sensitivity, compared to conventional dental bleaching compositions.

Such compositions and methods for bleaching and whitening teeth, while reducing tooth sensitivity, are disclosed and claimed herein.

BRIEF SUMMARY AND OBJECTS OF THE INVENTION

The present invention generally relates to dental whitening compositions and methods for whitening teeth. In addition, the present invention relates to compositions and methods that result in reduced tooth sensitivity compared to conventional dental bleaching compositions. The compositions of the present invention include a dental bleaching agent in combination with potassium nitrate ($KNO_3$), which acts as a desensitizing agent.

The potassium nitrate and bleaching agent are typically dispersed in a liquid or gel carrier. In addition, the whitening compositions may include one or more other dental agents, such as an anticariogenic agent for reinforcing teeth against tooth decay or an antimicrobial agent for treating gum diseases. The most commonly used anticariogenic agents include fluoride salts, such as stannous or sodium fluoride, which can also impart antidemineralization or even remineralization properties to the tooth whitening compositions. Examples of preferred antimicrobial agents include chlorohexidine, tetracycline, cetyl pyridinium chloride, benzalkonium chloride, cetyl pyridinium bromide, methyl benzoate, and propyl benzoate.

The compositions are preferably substantially free of abrasives, as the compositions are typically not scrubbed onto the teeth. When using abrasive toothpastes, people typically brush for less than 60 seconds, which is not enough time to cause a noticeable whitening effect. On the other hand, scrubbing teeth with an abrasive material for an extended period of time can be harmful to the tooth enamel. Therefore, in order to allow for extended bleaching and whitening of teeth, the inventive compositions will preferably not include substantial quantities of an abrasive.

The compositions are preferably used with a dental tray that is thin-walled, flexible and lightweight. Preferred dental trays should be adapted for maximum comfort and will exert little, if any, significant mechanical pressure onto the person's teeth or gums. When using a tray of this nature, the tooth whitening compositions of the present invention will preferably be sufficiently sticky, viscous and resistant to dilution by saliva so as to act as a glue-like material and reliably adhere and retain the dental tray over the person's teeth for a desired time duration. Although such dental trays are preferred, any conventional dental trays may also be utilized. The inventive dental compositions may also be applied directly to a person's teeth without using a tray. In such cases, higher concentrations of the active bleaching agents will preferably be used in order to speed up the desired bleaching action.

Any component other than the active dental agents, such as the potassium nitrate, bleaching agent, antimicrobial agent and anticariogenic agent, shall comprise the "carrier". In the case where the dental composition is sticky and viscous, the carrier will constitute a sticky matrix material formed by combining a sufficient quantity of a tackifying agent, such as carboxypolymethylene, with one or more solvents, such as glycerin, polyethylene glycol, or water. Although the carrier is preferably formed by combining a tackifying agent and a solvent, the carrier may comprise a solvent without a tackifying agent in some embodiments. Preferred compositions, as described hereinbelow, are relatively sticky and glue-like to enable a preferred dental tray to be held and retained against a person's teeth. Preferred carriers are preferably safe for oral use, do not readily dissolve in saliva, and do not react with active agents.

In addition to carboxypolymethylene, examples of other suitable tackifying agents, or thickening agents that can assist other tackifying agents, include xanthan gum, talha gum, tragacanth gum, carboxymethylcellulose, locust bean gum, guar gum, Irish moss gum, ghatti gum, furcelleran gum, carrageenan gum, arabic gum, alginic acid gum, agar gum, alginate gum, proteins, such as collagen, PEMULEN®, a proprietary compound of B.F. Goodrich, POLYOX®, a mixture of polyethylene oxides having a molecular weight of 100,000-8,000,000 and available from Union Carbide, including higher molecular weight polyethylene glycols, or any compositional or chemical equivalents of the foregoing. PEMULEN® is a propriety formula that includes a significant quantity of a polyacrylic copolymer that has a slightly hydrophobic end and a strongly hydrophilic end.

In addition to glycerin, many other polyols may serve as suitable solvents. The solvent may also be water alone or in combination with a polyol. Glycerin is a preferred solvent as it works well in forming a sticky gel with carboxypolymethylene. Glycerin also provides some flavor enhancement. A few possible substitutes for glycerin include propylene glycols, polypropylene glycol, polyethylene glycols, eryrthritol, sorbitol, mannitol, other polyols, and the like. In some embodiments polyols such as glycerin, lower molecular weight polyethylene glycols, polypropylene glycol, propylene glycol, and sorbitol may also be used without a tackifying agent.

As indicated hereinabove, one currently preferred sticky matrix material includes a mixture of carboxypolymethylene together with other suitable admixtures. The term "carboxypolymethylene" is used to denote a broad category of polymers, particularly copolymers of acrylic acid and polyallyl sucrose. Because carboxypolymethylene that has not been completely neutralized includes active carboxylic acid groups or moieties, carboxypolymethylene can be classified as a weak acid. When dispersed in water, carboxypolymethylene can have a pH as low as about 2.5.

Because highly acidic compositions can etch teeth, it is generally preferable to adjust the pH of dental compositions that include carboxypolymethylene or other acids to make them less acidic. Accordingly, it is preferable to adjust the pH of the bleaching compositions to within a range from about 4 to about 9, more preferably to within a range from about 5 to about 8. Because it is contemplated that the carboxypolymethylene used in the matrix material and the compositions of the present invention will be mixed with a base to raise the pH of the resulting dental composition, for purposes of the specification and the appended claims, the term "carboxypolymethylene" shall include carboxypolymethylene within compositions at any pH. Preferred bases used to adjust the pH of the dental compositions may include inorganic bases such as sodium hydroxide or ammonium hydroxide. Alternatively, the base may include an organic base such as triethanolamine or other organic amines.

Since peroxides may cause irritation and also greater sensitivity in teeth for some people, the simultaneous inclusion of potassium nitrate can offset the potentially negative effects of the peroxide. Accordingly, potassium nitrate provides for desensitization. Other desensitizing agents can also be used to desensitize teeth, including citric acid, citric acid salts, strontium chloride, and the like. Fluoride salts, when used in combination with a peroxide dental bleaching agent, have also been found to inherently offset tooth sensitivity that may be caused by the peroxide bleaching agent. Since the present invention allows for prolonged contact via the use of an appropriate tray and/or a sticky composition, the potassium nitrate is preferably included in an amount of about 0.01% to about 2% by weight of the dental composition, and more preferably in an amount of about 0.05% to about 1% by weight. Surprisingly, dental bleaching compositions that include only 0.5% potassium nitrate have been found to be far superior to compositions that include 3% potassium nitrate in desensitizing teeth.

In a preferred embodiment, the dental compositions within the scope of the present invention will be sufficiently sticky and generally viscous such that positive pressure is needed to dispense them from the container; gravity is not sufficient. Unlike conventional low-viscosity compositions such as GLY-OXIDE (manufactured by Marion Laboratories) or PROXIGEL (manufactured by Reed and Carnick according to U.S. Pat. No. 3,657,413 to Rosenthal), preferred whitening compositions according to the present invention will be packaged within a syringe, squeezable tube, or other similar positive pressure dispensing device.

An improved dental tray that is thin-walled, flexible and lightweight for holding the dental composition adjacent to a person's teeth is preferably used in combination with sticky and viscous dental whitening compositions of the present invention. The general process for preparing such dental trays is as follows. First, an alginate impression which registers all teeth surfaces plus the gingival margin is made and a stone cast is made of the impression. Optional reservoirs can be prepared by building a layer of rigid material on the stone cast on specific teeth surfaces to be treated. A dental tray is then vacuum formed from the modified cast using a thin, flexible plastic sheet material. Once formed, the tray is preferably trimmed barely shy of the gingival margin on both the buccal and lingual surfaces of the person's teeth. The resulting tray provides a comfortable fit of the person's teeth, with optional reservoirs or spaces located where the rigid material was placed on the stone cast. The trays can optionally overlap the gums if desired to provide contact between the dental compositions and a person's gums. The trays of the present invention have greatly increased comfort and exert little or no significant mechanical pressure on a person's teeth or gums. Instead, sticky dental compositions within the scope of the invention can act like a glue to hold the improved trays in place.

The amount of tooth whitening obtained through the use of the inventive compositions and methods is dependent primarily upon (1) the length of time each day the tray is worn; and (2) the number of days the tray is worn. The treatment schedule may be tailored to each person's lifestyle or response to the treatment and can be performed as often as a person desires to provide effective relief from excessively translucent teeth. It has been found that treatment during sleep is a good treatment period since there is less mouth activity which causes less whitening composition to be pumped from the tray.

In short, the desensitizing bleaching compositions according to the invention include a dental bleaching agent (e.g., carbamide peroxide) in an amount so as to effect bleaching of a person's teeth, typically by maintaining the dental composition in contact with the person's teeth for at least about 15 minutes, more preferably for at least about 1 hour. They also include potassium nitrate in an amount so as to both reduce sensitivity that may be caused by contacting the dental bleaching agent with a person's teeth and also to enhance the whitening effect of the dental bleaching agent. By means of a comparative study discussed below, the inventors discovered the surprising and unexpected result that the desensitization and enhanced whitening properties of potassium nitrate are actually higher when included in lower concentrations (e.g., 0.5%) rather than at higher concentrations (e.g., 3%). Fluoride salts, when used in combination with a peroxide dental bleaching agent, have also been found to inherently offset tooth sensitivity that may be caused by the peroxide bleaching agent.

Moreover, the compositions of the present invention should be contrasted with conventional desensitizing tooth paste compositions formulated with large quantities of abrasives (e.g., 20% or more by weight) and high concentrations of potassium nitrate (e.g., up 10% by weight) which are intended to contact the teeth during daily brushing (typically for 60 seconds or less). Such compositions are formulated to treat past, rather than prospective, tooth sensitivity. They do not treat sensitivity caused by simultaneous contact of the teeth with a dental bleaching agent, particularly since no significant bleaching and sensitization of a person's teeth are likely using peroxide-containing toothpastes due to the extremely short contact times.

Accordingly, an object of the present invention is to provide improved compositions and methods for whitening teeth.

It is another object to provide compositions for whitening teeth which reduce tooth sensitivity compared to conventional dental bleaching compositions.

These and other objects and features of the present invention will become more fully apparent from the description as follows, or may be learned by the practice of the invention.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings, in which:

FIG. 1 is a perspective view of a stone cast of a person's teeth with a coating being applied to selected teeth surfaces;

FIG. 2 is a perspective view of the stone cast of FIG. 1 with a dental tray formed from the cast and trimmed below the gingival margin;

FIG. 3 is a cross-sectional view taken along line 3-3 of FIG. 2;

FIG. 3A is an enlarged close-up view taken within the section line 3A-3A of FIG. 3;

DETAILED DESCRIPTION OF THE PREFERRED EMBODIMENTS

Figure 4:
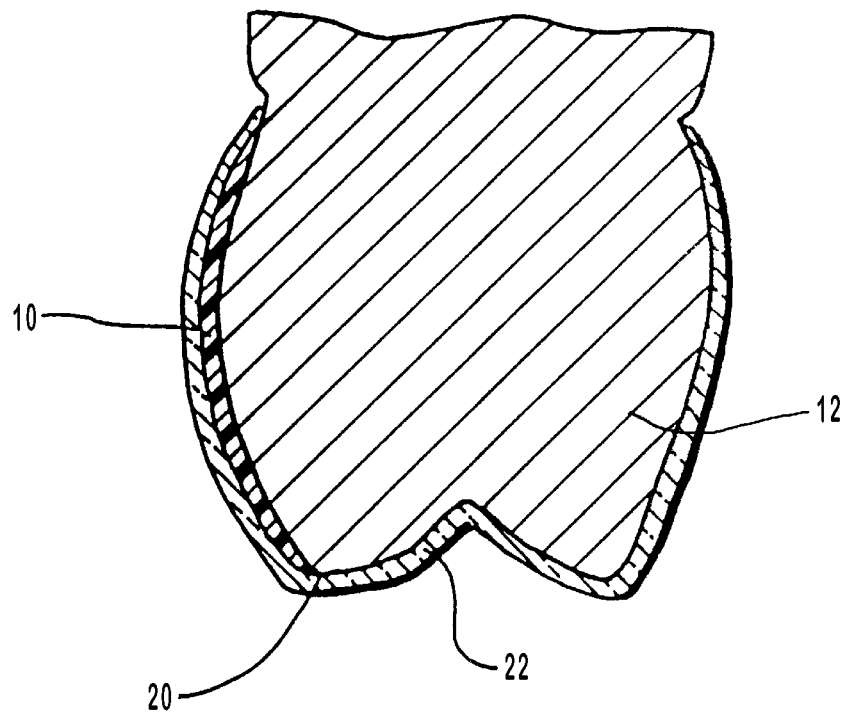
FIG. 4 is a cross-sectional view taken along line 4-4 of FIG. 2.

As summarized above, the present invention generally relates to dental bleaching compositions and methods for whitening teeth, while also minimizing or eliminating tooth sensitivity. At a minimum, the inventive compositions will include a dental bleaching agent and potassium nitrate, which acts as a desensitizing agent. The bleaching agent and potassium nitrate are delivered to the teeth by means of a carrier, preferably a carrier that is a sticky matrix. Although potassium nitrate is known as an effective desensitizing agent when used in toothpastes at higher concentrations (e.g., 5% or more), it has surprisingly been found that its effectiveness as a desensitizing agent when used in combination with a dental bleaching agent actually increases when used in very low concentrations (e.g., about 0.01% to about 2%). The compositions preferably do not include an abrasive.

In a preferred embodiment, the dental whitening compositions will be used in conjunction with a thin, flexible, comfortable-fitting dental tray in order to hold the compositions against the person's teeth. Preferred dental trays will conform to the size and shape of a person's teeth and will exert little or no significant mechanical pressure onto the person's teeth and/or gums. This makes them more comfortable and pleasant to use compared to conventional dental trays. Nevertheless, the inventive tooth whitening compositions may certainly be used with conventional dental trays, or with no tray at all.

In the case where a thin, flexible dental tray is used, the potassium nitrate, dental bleaching agent and optional dental agents will preferably be dispersed in a sticky matrix material capable of exerting a glue-like action such that the whitening composition can adhere and retain the tray in place over a person's teeth without significant mechanical pressure by the tray. The tooth whitening/desensitizing compositions may alternatively be placed directly onto the person's teeth without a tray, or by means of conventional dental trays that are held in place by mechanical fit.

The amount of potassium nitrate that is included within the whitening compositions of the present invention may vary depending on the duration that the composition will be in contact with the person's teeth. When used with dental bleaching compositions that are intended to come into prolonged contact with a person's teeth, such as dental regimens in which a person applies the composition on a daily basis over an extended period of time, the concentration of potassium nitrate is preferable in a range of about 0.01% to about 2% by weight of the dental composition, and more preferably in a range of about 0.05% to about 1% by weight. On the other hand, for one-time applications, particularly for shorter periods of time (i.e., one hour or less), the concentration of the potassium nitrate can be increased, even up to 10% or more.

For repeated and prolonged usage, lower concentrations of $KNO_3$ are better at desensitizing, perhaps because $KNO_3$, while an anesthetic in lower dosages, may become an irritant at higher dosages.

In a preferred embodiment, the carrier will include a tackifying agent and a solvent, which together yield a sticky matrix material, although a solvent may be used alone in some embodiments. The sticky matrix material will be sufficiently sticky to enable a preferred dental tray to be held and retained against a person's teeth. Various tackifying agents will be described hereinbelow.

Suitable sticky matrix materials are preferably safe for oral use and do not inactivate the potassium nitrate. They are preferably viscous and do not readily dissolve in saliva. One currently preferred tackifying agent used to form a sticky and viscous matrix material is carboxypolymethylene. Carboxypolymethylene can be used to form a glue-like dental whitening composition that can itself act as an adhesive in holding a comfortable, non-self-retaining dental tray against a person's teeth. The use of carboxypolymethylene, either alone or in combination with other tackifying agents, eliminates the need to use dental trays that are self-retaining (i.e., typically trays that are rigid, which mechanically interlock over a person's teeth or gums, and which are intended for use with less sticky compositions).

Carboxypolymethylene is a broad term that refers to vinyl polymers having active carboxyl groups. Suitable carboxypolymethylene compositions may be obtained from B. F. Goodrich Company under the trade name CARBOPOL®. Another tradename for carboxypolymethylene is CARBOMER®. In a commonly-sold form, carboxypolymethylene can have a pH as low as 2.5. As discussed below, the pH of compositions made with carboxypolymethylene can be raised to yield compositions that are less acidic.

One currently preferred carboxypolymethylene resin is known by the tradename CARBOPOL 934P. CARBOPOL 934P is a high purity pharmaceutical grade of CARBOPOL 934, having an approximate molecular weight of about 3,000,000. In addition to thickening and suspending, CARBOPOL 934P has been used in dry tablets to impart sustained release properties. Extensive toxicity studies have been conducted on CARBOPOL 934P, and a master file has been established with the Food and Drug Administration. It is listed as CARBOMER 934P in the National Formulary. A more recently preferred carboxypolymethylene is CARBOPOL 974P NF, which has more recently surpassed CARBOPOL 934P as the carboxypolymethylene of choice. Although CARBOPOL 974P NF is similar or identical in molecular weight compared to CARBOPOL 934P, it is purified in a way that makes it more pharmaceutically acceptable material.

It is believed that other carboxypolymethylene resins, such as CARBOPOL 940, may be substituted for CARBOPOL 934P or CARBOPOL 974P NF. CARBOPOL 934P and CARBOPOL 974P NF are currently preferred because they are obtainable in a pharmaceutical grade.

The amount of carboxypolymethylene within the inventive dental whitening compositions can vary depending on the desired level of stickiness and also the identities and amounts of the other components within the dental composition. In general, the dental whitening/desensitizing compositions of the present invention will preferably include carboxypolymethylene in a concentration in a range from about 0.5% to about 25% by weight of the dental whitening composition, more preferably in a range from about 2% to about 12% and most preferably in a range from about 3% to about 10%. Where is it desired to increase the stickiness, viscosity and resistance to dilution to saliva, one may adjust the concentration of carboxypolymethylene to achieve a desired level of any or all of these properties. Increased stickiness assists in retaining the preferred dental trays against a person's teeth. Alternatively, compositions can be made less adhesive and tacky if desired, particularly is applied directly without a dental tray.

It should be understood, however, that the actual amount of carboxypolymethylene is not critical for obtaining a sticky, viscous dental composition. For example, the sticky matrix material may include other tackifying components that in combination with, or in lieu of some or all of, the carboxypolymethylene will yield a dental whitening composition having the desired level of stickiness needed to hold a preferred, comfortable-fitting dental tray in place over a person's teeth. Other synthetic polymers and/or natural gums, proteins, or other gel-forming admixtures can be used so long as they yield a sticky dental whitening composition.

In order to obtain good dispersion of the carboxypolymethylene resin within the dental whitening composition, it is recommended that the carboxypolymethylene be mixed with a suitable solvent before attempting to add other components that are less compatible with carboxypolymethylene, such as water. Examples of suitable solvents for use with carboxypolymethylene include glycerin, polyalkylene glycols, other polyols, and the like. Glycerin appears to enable larger quantities of carboxypolymethylene to be dispersed in water. It is preferable that the concentration of glycerin, polyol, or like substance utilized as a solvent in the dental whitening compositions be added in a range from about 15% to about 85% by weight of the dental whitening compositions, more preferably in a range from about 25% to about 75% by weight, and most preferably in a range from about 30% to about 65% by weight.

Glycerin, other polyols, and the like are inexpensive solvents that work well in forming a sticky gel with carboxypolymethylene. The glycerin also provides some flavor enhancement such that a bland, sweet flavor is perceived. A few possible substitutes for glycerin include propylene glycol, polypropylene glycol, polyethylene glycols, sorbitol, mannitol, eryrthritol, other polyols, stearyl alcohol and other alcohols, and the like. Ethylene glycol would also work but is disfavored since it is toxic. In addition to acting as a solvent for the tackifying and thickening agents, hydrophilic solvents such as glycerin, polyethylene glycols, polypropylene glycol, propylene glycol, and sorbitol may also be used as a suitable carrier without a tackifying agent.

Water may also be included as a solvent within the compositions of the present invention, although more carboxypolymethylene or other tackifying agent must generally be included as more water is included in order to maintain the same level of stickiness. The amount of water included within the dental whitening compositions of the present invention is preferably in a range of about 0% to about 50% by weight of the dental whitening composition, more preferably in a range of about 1% to about 45% by weight and most preferably in a range of about 2% to about 40% by weight. It will be appreciated that the total quantity of water in the dental whitening composition may come from different sources. For instance, some constituents such as dental agents and bases discussed below may come as aqueous solutions.

Because carboxypolymethylene is a polycarboxylic acid, it tends to lower the pH of the resulting dental whitening compositions significantly, down to a pH of about 2.5 in some cases. Although measuring the pH in anhydrous compositions is generally meaningless, the theoretical pH becomes relevant when an anhydrous dental composition is applied to a person's teeth, which are bathed in water-containing saliva.

It appears, based upon clinical and in vitro testing, that dental whitening compositions with a pH below about 5 are able to etch enamel. To avoid etching enamel, it is preferable to add a neutralizing agent, or more specifically, a base in order to raise the pH of the inventive dental whitening compositions to within a pH range of about 4 to about 9, preferably to within a range of about 5 to about 8, and most preferably a pH from about 6 to about 7.

Inorganic and organic bases may be used to raise the pH, with the use of concentrated aqueous sodium hydroxide (50% NaOH in water) being one currently preferred embodiment. In addition to sodium hydroxides, other inorganic bases may be used such as potassium hydroxide and ammonium hydroxide. Examples of suitable organic bases include alkyl amines such as triethanolamine, di-isopropanol amine and other similar amines. The amount of neutralizing agent or base to be included will generally depend on the desired pH and the amount of carboxypolymethylene in the dental whitening composition. Accordingly, neutralizing agents or bases are preferably included in a range from about 1% to about 12% by weight of the dental whitening composition, more preferably in a range from about 2% to about 8% by weight and most preferably in a range from about 3% to about 7% by weight.

The term "carboxypolymethylene" shall be understood to include carboxypolymethylene resins regardless of the pH of the overall dental composition. In other words, the term "carboxypolymethylene" broadly includes resins that have been mixed with a base to raise the pH of the compositions. Moreover, the term "carboxypolymethylene" shall broadly include carboxypolymethylene resins that have reacted with, formed complexes with, or otherwise been altered in any way by other components within the dental whitening compositions of the present invention so long as the carboxypolymethylene or mixture product thereof is able to impart the desired level of stickiness and viscosity to the final dental whitening composition in combination with the other components within the dental whitening composition.

In addition to carboxypolymethylene, examples of other suitable tackifying and thickening agents include gums such as xanthan gum, talha gum, tragacanth gum, locust bean gum, guar gum, Irish moss gum, ghatti gum, furcelleran gum, carrageenan gum, arabic gum, alginic acid gum, agar gum, and alginate gum, as well as proteins, such as collagen, or cellulosic ethers. Another suitable tackifying agent is sold as PEMULEN®, a proprietary compound from B.F. Goodrich, or a compositional or chemical equivalent thereof. PEMULEN® includes a significant quantity of a polyacrylic copolymer that has a slightly hydrophobic end and a strongly hydrophilic end. Additional examples of suitable tackifying agents include polyethylene oxides such as POLYOX® sold by Union Carbide. These tackifying agents may be present in the same ranges as discussed above in relation to carboxypolymethylene.

Examples of suitable bleaching agents include aqueous hydrogen peroxide, carbamide peroxide, benzoyl peroxide, glyceryl peroxide, percarbonates and perborates of alkali and alkaline earth metals (e.g., sodium perborate) and peroxyacetic acid. A significant advantage of using potassium nitrate as an opacifying agent in combination with a bleaching agent in a tooth whitening composition is that the potassium nitrate simultaneously decreases the sensitivity of the teeth that may result from the use of the bleaching agent. The bleaching agents are preferably included in a range from about 0.5% to about 50% by weight of the dental whitening composition, more preferably in a range from about 1% to about 30% by weight and most preferably in a range from about 3% to about 20% by weight.

In order to preserve the stability of the dental whitening compositions, it is often preferable to include an ion scavenger such as EDTA, salts of EDTA such as edetate disodium, oxine EDTA, calcium disodium EDTA, and others. Additionally, ion scavengers such as citric acid, succinic acid, adipic acid, nitrates and phosphates of tin and any other commonly-used chelating agents may be used. Ion scavengers are preferably included in an amount in a range from about 0% to about 1% by weight of the dental whitening composition, more preferably in a range from about 0.03% to about 0.5% by weight and most preferably in a range from about 0.05% to about 0.2% by weight.

It may also be preferable to include other active dental agents to provide other types of dental and/or gum treatment. For example, in conjunction with dental desensitization and/or opacification, it may be desired to provide an anticariogenic treatment. Preferred anticariogenic and antidemineralizing agents include fluoride salts, more particularly sodium monofluorophosphate, sodium fluoride, and stannous fluoride. Depending on the level of fluoride treatment desired, and depending on whether or not a composition is "over-the-counter" or "by prescription", the fluoride will be included in a range from about 0% to about 1% by weight of the dental whitening composition, more preferably in a range from about 0.1% to about 0.5% by weight. Fluoride salts, when used in combination with a peroxide dental bleaching agent in such amounts, have also been found to inherently offset tooth sensitivity that may be caused by the peroxide bleaching agent.

Antimicrobial agents, e.g., for fighting gum disease, may be included in conjunction with the potassium nitrate or other opacifying agent. Examples of useful antimicrobial agents include chlorohexidine, tetracycline, cetyl pyridinium chloride, benzalkonium chloride, cetyl pyridinium bromide, methyl benzoate, and propyl benzoate. The antimicrobial agents are preferably included in an amount in a range from about 0% to about 15% with the dental whitening composition, more preferably in a range from about 1% to about 5% by weight.

As indicated hereinabove, the dental whitening compositions of the present invention preferably do not include an abrasive. Abrasives only externally treat a tooth; however, it is believed that whitening of a tooth is achieved by the action of the bleaching agent internally within a tooth. Not only are abrasives unnecessary but inclusion of abrasives in the composition may be undesirable in preferred embodiments where it is desired for the whitening composition to remain on the teeth for an extended period of time (i.e., greater than about 3 minutes). In any event, it is common experience that toothpastes become quickly diluted by saliva and will not persist in a paste-like form for more than a short period of time (i.e., for more than about a minute).

Other suitable tooth desensitizing agents that may be used in addition to potassium nitrate according to the present invention include citric acid, citric acid salts, strontium chloride, and the like, as well as other desensitizing agents known in the art. Fluoride salts, when used in combination with a peroxide dental bleaching agent, have also been found to inherently offset tooth sensitivity that may be caused by the peroxide bleaching agent. The amount of desensitizing agent included within the dental whitening compositions of the present invention may vary according to the concentration of the potassium nitrate, the desired strength and intended treatment times. Accordingly, if included at all, the other desensitizing agents will preferably be included in an amount in a range from about 0.1% to about 10% by weight of the dental desensitizing composition, more preferably in a range from about 1 to about 7% by weight.

One currently preferred method of dispensing preferred sticky and viscous dental whitening compositions within the scope of the present invention is by means of a syringe. Squeezable tubes and other similar dispensing devices may also be used to dispense the compositions. Upon dispensing, preferred dental whitening compositions are sufficiently viscous that they do not easily settle or spread once dispensed, but will generally remain as a single extruded strand or bead of dental whitening composition. Nevertheless, bottles, tubes or other dispensing means known in the art may be used, particularly where the whitening composition has lower viscosity, low stickiness, and/or does not include a thickening agent.

It is currently preferred to provide a unit dose of the dental whitening compositions in a syringe or similar dispensing device. In this way, the person can load the precise amount of dental whitening composition onto the dental tray for each treatment period. By using such dispensing devices, the dentist is also able to monitor how many doses the person has received and used.

Although not required, sticky and viscous dental whitening compositions of the present invention are preferably used to treat a person's teeth in conjunction with dental trays that exert little or no significant mechanical pressure onto a person's teeth and gums. The result is a more comfortable and pleasant feeling dental tray, unlike prior art dental trays which are generally rigid and/or thick-walled such that they exert sufficient mechanical pressures onto the teeth and/or gums to be "self-retaining".

In the general process for preparing preferred dental trays according to the present invention, an alginate impression is made which registers all teeth surfaces plus the gingival margin. Thereafter, a stone cast is made of the impression. Excess stone can be trimmed away for easy manipulation and forming the dental tray.

Reference is now made to FIGS. 1-4. In a preferred method for forming a dental tray, one or more reservoirs can be formed in the resultant dental tray by applying a thin coating 10 of a rigid material to the stone cast 12 corresponding to teeth where it is desired to provide more of the dental whitening composition. As depicted in FIG. 1, the coating 10 may be applied using a brush tipped applicator 14. The coating may be light curable for convenience. In those instances where the dental tray is to be trimmed below the gingival margin, the coating material will preferably be applied in a manner that is kept at a distance greater than about 1 mm from the gingival line 16 represented on the stone cast, more preferably in a range from about 1.25 to about 1.5 mm from the gingival line 16.

The finished coating will have a thickness corresponding to the desired reservoir depth, which will commonly be about 0.5 mm. It is generally preferred that the rigid coating material not be applied over the stone cast corresponding to the incisal edges 18 and occlusal edges 20 of the person's teeth. This because it is preferable for the incisal edges and occlusal edges of the person's actual teeth to contact the finished tray in order to prevent or reduce vertical movement of the tray during use, which movement could act as a pump that could express the dental whitening composition from the tray and result in the intake of saliva within the dental tray.

A dental tray 22 is then vacuum formed from the stone cast using conventional techniques. The dental tray 22 is preferably constructed of a soft transparent vinyl material preferably having a preformed thickness in a range from about 0.2 mm to about 1.5 mm, more preferably in a range from about 0.25 mm to about 1 mm. Soft materials yield dental trays that are more comfortable for the patient to wear. It will be appreciated that the final tray thickness may vary depending on the technique used to prepare the tray, as well as the size and shape of the person's teeth. Patients suspected of being breuxers or hard biters may require either a thicker or a harder material. Of course, patients should be counselled not to eat with trays in place or to bite firmly into them.

Once formed, the dental tray 22 is preferably trimmed barely shy of the gingival margin 16 of the person's teeth on both the buccal and lingual surfaces for maximum comfort. Enough tray material should be left to assure that the teeth will be covered to within about ¼ mm to about ⅓ mm of the gingival border upon finishing and beveling of the tray periphery. It is also generally preferred to scallop up and around the interdental papilla so that the finished tray does not cover them. The tray edges are preferably smoothed so that the lip and tongue will not feel an edge prominence. Slight adjustments to the tray may be made by carefully heating and stretching the tray material.

Figure 5:
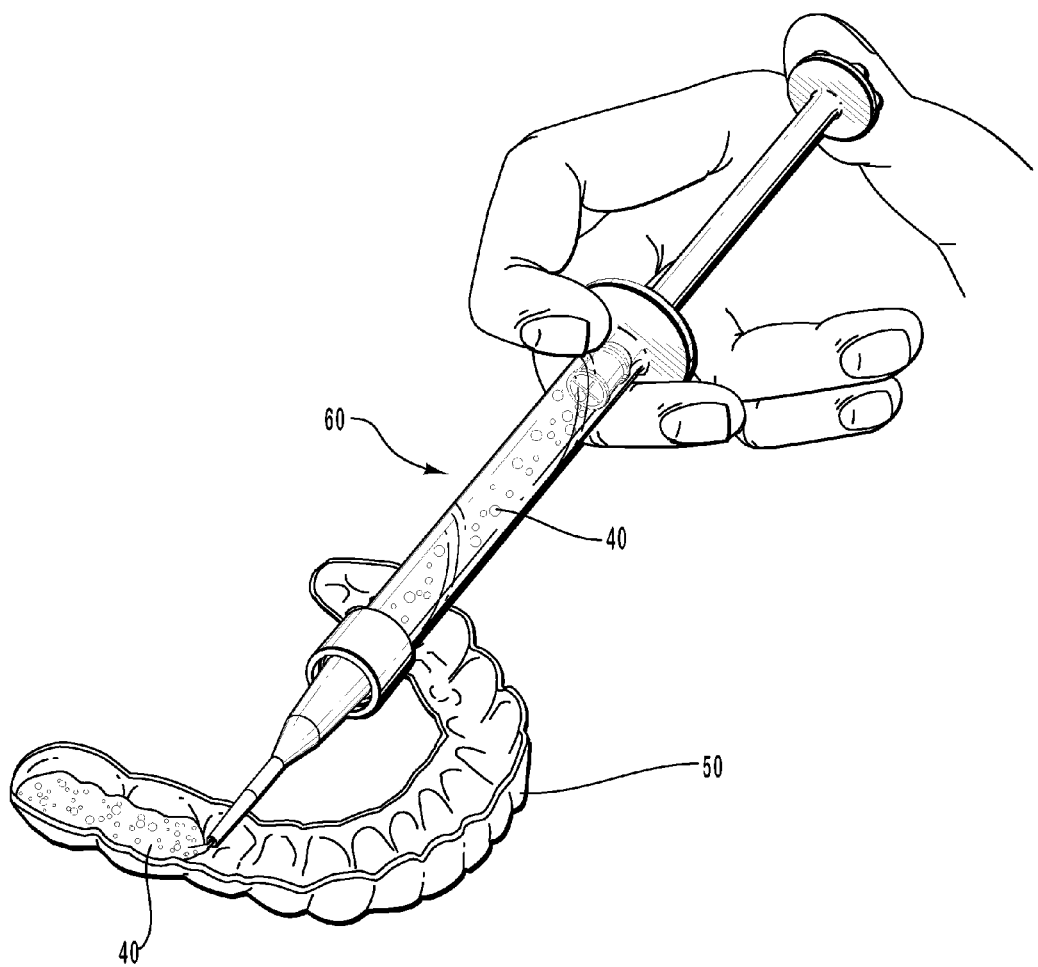
FIG. 5 is a perspective view of the opacifying composition being delivered from a syringe into a thin-walled, flexible dental tray.
Figure 6:
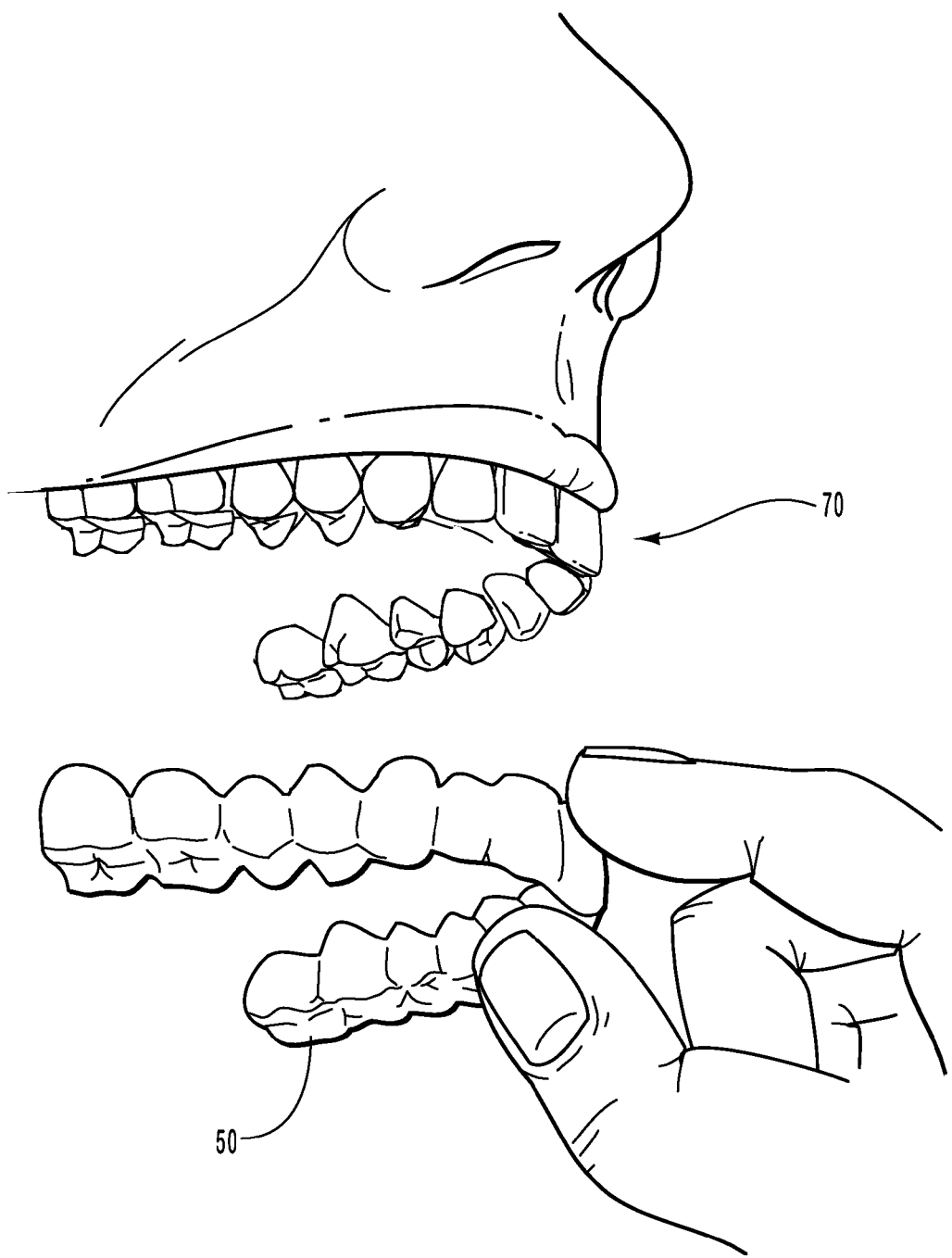
FIG. 6 is a perspective view of a thin-walled, flexible dental tray filled with the opacifying composition just before being positioned on a person's upper arch.
Figure 7:
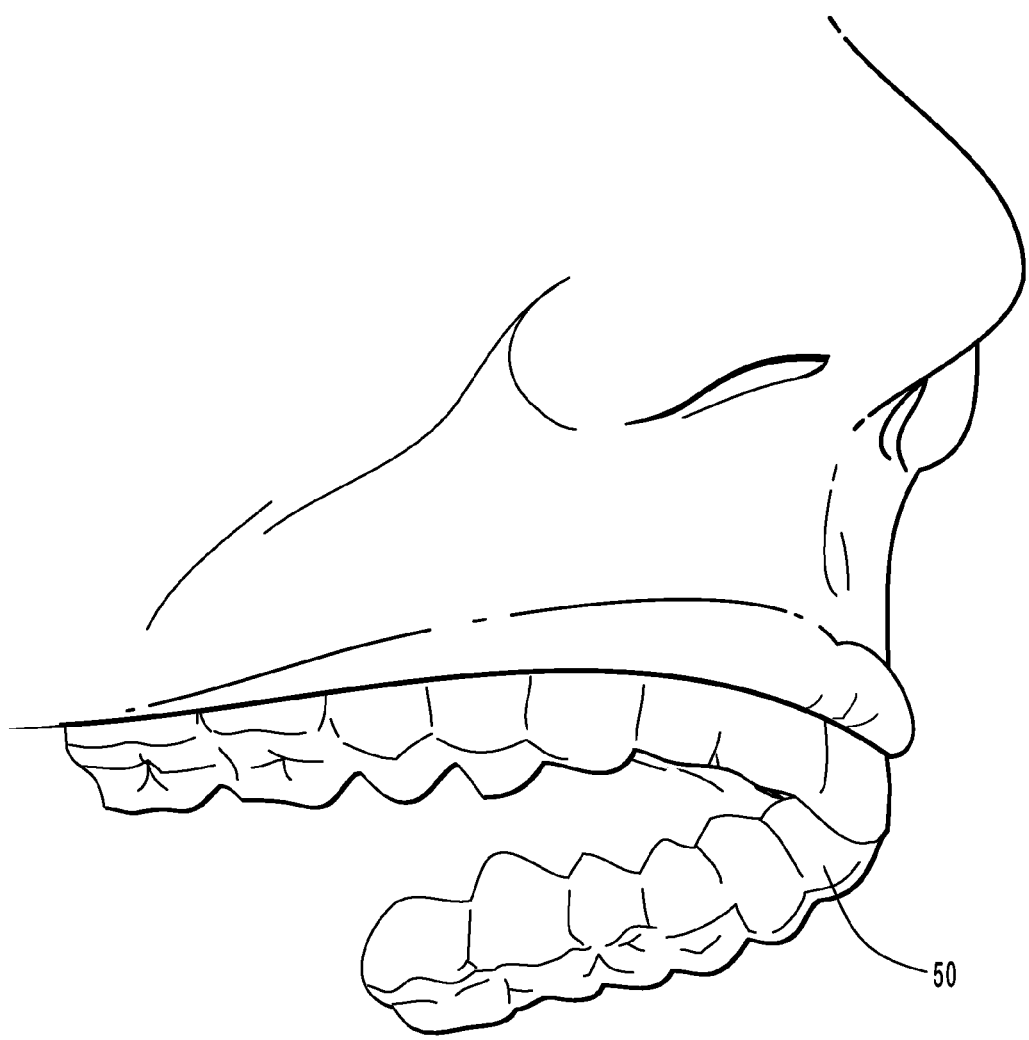
FIG. 7 is a perspective view of a thin-walled, flexible dental tray filled with the opacifying composition positioned on a person's upper arch.

Reference is now made to FIGS. 5-7. FIG. 5 depicts the dental whitening/desensitizing composition 40 being deposited into a dental tray 50 from a syringe 60. FIG. 6 depicts dental tray 50 being inserted onto an arch 70 in a patient's mouth. FIG. 7 depicts dental tray 50 in position on the teeth of arch 70. The dental composition may be deposited throughout the dental tray to contact the entire arch or may be deposited within a portion of the tray to only contact a portion of the arch. Additionally, the dental tray may be configured to only contact a portion of an arch or only a single tooth. While depositing the dental whitening composition into dental tray 50 as shown in FIG. 5 is the preferred method, the dental whitening composition may also alternatively be deposited directly onto the teeth and then tray 50 may be positioned on the teeth of arch 70.

From practice, it has been found that patients may experience less tooth discomfort from tray pressures when using a tray with reservoirs built into the tray as described above. It is currently believed this is due to the fact that the teeth are not held as firmly by the tray, so "orthodontic" pressures experienced by teeth from tray discrepancies are minimized. The use of thin, soft tray materials minimizes mechanical forces applied to teeth or gums compared to the harder or thicker plastics known in the art. Reservoirs, of course, can provide more of the dental whitening composition against the person's teeth and can also assist in seating the dental tray over the person's teeth.

Although the aforementioned thin, flexible dental trays are preferred when treating a person's teeth, it may be preferable in some cases to allow the dental tray to overlap the person's gums in the case where dental agents are included to fight gum diseases. Of course, to the extent that the dental whitening compositions do not irritate the gums, the dental trays can always be constructed to overlap the gums.

Nevertheless, it has been found that where it is desired to treat a person's teeth rather than the gums, it is generally more comfortable for the patient if the dental tray has been trimmed to or below the gingival margin. Even in those cases where the dental trays will overlap the person's gums, the dental trays of the present invention preferably will not exert significant mechanical pressure onto the person's gums.

Accordingly, the dental whitening compositions will preferably have a stickiness such that they can reliably adhere and retain a dental tray over a person's teeth for at least about one hour without significant mechanical pressure from the dental tray, more preferably for at least about two hours, and most preferably for at least about four hours. Nevertheless, while the foregoing time durations are given in order to provide an accurate measurement of the stickiness of the dental whitening compositions of the present invention, they should not be taken to be a limitation as to the actual length of time that the patient may wish to use the inventive dental whitening compositions. While a given dental whitening composition may be able to retain the dental tray against a person's teeth for, e.g., 10 hours or more, that composition could certainly be used within the scope of the present invention for any desired time period, such as for 15 minutes, one hour, or any desired time duration.

The desensitizing dental whitening compositions of the present invention may be used at any time and for any duration by a person that desires to whiten his or her teeth. Although the dental whitening compositions of the present invention facilitate the use of flexible, thin-walled dental trays that are more comfortable to use compared to prior dental trays, the insertion of any dental tray within a person's mouth will cause some alteration of behavior and diminution of the freedom to use one's mouth. Therefore, in order to maximize treatment time and reduce the inconvenience of having a dental tray lodged within a person's mouth, it is recommended to use the dental trays at night during a person's sleep.

It has been found that optimal results are achieved from cyclic exposure periods involving repeated exposures over several days or weeks. For example, the treatment regime may alternatively entail exposure for a period of time such as an hour without further exposure until the subsequent day. For day use, it is recommended that the whitening compositions be applied for about 1 to 3 hours. The length of the treatment period during night use may vary with the sleep pattern of the particular person and may accordingly be between about 5 to 9 hours.

In order to more clearly illustrate the parameters of the inventive dental whitening compositions within the scope of the present invention, the following examples are presented. The following examples are intended to be exemplary and should not be viewed as limiting to the scope of the invention.

EXAMPLE 1

A whitening composition within the scope of the invention was prepared by combining the following ingredients in the following proportions, measured as percentage by weight of the whitening composition:

| | |
|---|---|
| CARBOPOL 974P NF | 6.8% |
| Glycerin | 48.45% |
| Polyethylene glycol 300 | 5.5% |
| Water | 20.0% |
| Sodium hydroxide (50%) | 5.4% |
| KNO3 | 3.0% |
| Carbamide peroxide | 10.5% |
| Disodium EDTA | 0.1% |
| NaF | 0.25% |

The CARBOPOL 974P NF was obtained from B.F. Goodrich Company in Cleveland, Ohio. The CARBOPOL 974P NF was first combined with the glycerin and polyethylene glycol 300 then mixed with the water. Mixing glycerin and polyethylene glycol 300 within the CARBOPOL 974P NF enabled it to be more easily mixed with the water. The $KNO_3$, carbamide peroxide and disodium EDTA were added to the mixture, after which the sodium hydroxide was blended into the homogeneous composition in order to raise the pH to an acceptable level. The sodium fluoride was then added. The resulting dental whitening composition was found to have bleaching, desensitizing and anticariogenic properties, and was sufficiently sticky that it could reliably hold and maintain a dental tray against a person's teeth without significant mechanical pressure being exerted by the tray onto a person's teeth and gums.

EXAMPLE 2

A preferred dental whitening composition within the scope of the present invention was made according to the procedure of Example 1, except that the ingredients were combined in the following concentrations by weight percent:

| | |
|---|---|
| CARBOPOL 974P NF | 6.8% |
| Glycerin | 35% |
| Polyethylene glycol 300 | 5.5% |
| Water | 20% |
| Sodium hydroxide (50%) | 5.8% |
| KNO3 | 0.5% |
| Carbamide peroxide | 10.5% |
| Disodium EDTA | 0.3% |
| Peppermint Flavor | 0.6% |
| Xylitol | 15% |

The resulting dental whitening/desensitizing composition was tested and found to be surprisingly superior to test compositions similar to those of Example 1 that included 3% potassium nitrate. Compared to tooth whitening/desensitizing compositions that included 3% potassium nitrate, the 0.5% formulation of Example 2 exhibited greatly reduced tooth sensitivity. These included sensitivity to hot and cold, as well as general sensitivity of gums, tongue and throat. The 0.5% formulation of Example 2 also showed a dramatic increase in tooth whitening ability compared to a test composition that included no potassium nitrate, thus establishing the surprising result that potassium nitrate in minor concentrations greatly increases the whitening effect of the dental bleaching composition.

Comparative Study

The composition of Example 2 was the subject of a comparative study comparing the desensitizing and bleaching ability of the composition of Example 2 to four other dental bleaching compositions. In the study, the five dental compositions were labeled as compositions A-E, respectively, with composition E being the composition of Example 2. The dental bleaching compositions were applied using custom dental trays made to fit each patient. Compositions A-D were similar to the composition of Example 2, except that they included differing amounts of carbamide peroxide and potassium nitrate and, in one case, a different sweetener:

| Composition | Carbamide Peroxide | $KNO_3$ | Sweetener |
|---|---|---|---|
| A | 10% | 0% | Xylitol |
| B | 10% | 3% | Xylitol |
| C | 10% | 3% | Aspartame |
| D | 15% | 3% | Xylitol |

The results of the comparative study are set forth in Table 1.

TABLE 1

| 1 | 2 | 3 | 4 | 5 | 6 | 7 | 8 | 9 |
|---|---|---|---|---|---|---|---|---|
| A | 266 | 37 (13.9) | 40 (15) | 2 (0.8) | 3 (1.1) | 14 | 7 | 5.4 |
| B | 294 | 51 (17.3) | 50 (17) | 14 (4.8) | 3 (1) | 17 | 6 | 4.6 |
| C | 279 | 65 (23.3) | 45 (16.1) | 4 (1.4) | 3 (1.1) | 17 | 6 | 6.7 |
| D | 256 | 61 (23.9) | 70 (27.6) | 13 (5.1) | 2 (0.8) | 18 | 2 | 7.5 |
| E | 216 | 14 (5.3) | 4 (2.1) | 0 (0) | 0 (0) | 7 | 11 | 8.6 |

Column 1 = Composition Tested
Column 2 = Total number of days used by all patients in group
Column 3 = Number of days sensitive to hot or cold (% of total days)
Column 4 = Number of days gums sensitive (% of total days)
Column 5 = Number of days tongue sensitive (% of total days)
Column 6 = Number of days throat sensitive (% of total days)
Column 7 = Number of patients reporting sensitivity to anything
Column 8 = Number of patients reporting no sensitivity to anything
Column 9 = Average number of shade tab changes As clearly demonstrated by the data set forth in Table 1, the comparative study showed a dramatic decrease for composition E in the number of days that patients experienced hot or cold sensitivity compared compositions A-D. Surprisingly, even though potassium nitrate was heretofore believed to be a desensitizing agent at any concentration, when mixed with a dental bleaching agent at a concentration of 3% (compositions B-D), it actually increased patient tooth sensitivity compared to composition A, which included no potassium nitrate. This demonstrated that potassium nitrate, when blended with a dental bleaching agent and used, does not behave as a desensitizing agent but instead increases sensitivity at certain concentrations (e.g., 3%). Even more surprisingly, composition E resulted in an average Vita tab shade change of 8.6, which was even more than any of compositions A-D, including composition D, which included approximately 50% more bleaching agent than composition E, thus demonstrating the surprising result that including lower concentrations of potassium nitrate increases whitening of teeth compared to compositions that either include no potassium nitrate or those which include 3% potassium nitrate.

EXAMPLES 3-10

Dental whitening compositions within the scope of the present invention are made according to Example 1, except that the concentration of $KNO_3$ is included in the following amounts: 0.01%, 0.05%, 0.1%, 0.3%, 0.75%, 1%, 1.5% and 2%. The resulting dental bleaching compositions exhibit superior bleaching with less sensitivity compared to dental bleaching compositions that include no potassium nitrate. The resulting dental bleaching compositions also exhibit superior bleaching with less sensitivity compared to dental bleaching compositions that include 3% or more potassium nitrate blended with 10% or more carbamide peroxide.

EXAMPLE 11

Dental whitening compositions within the scope of the present invention are made according to Example 2, except that at least a portion of the glycerin is replaced by propylene glycol.

EXAMPLE 12

Dental whitening compositions within the scope of the present invention are made according to Example 2, except that the CARBOPOL 974 NF is included in the following amounts: 0%, 0.5%, 2%, 3%, 5%, 10% and 20%. The concentration of NaOH (50%) is adjusted accordingly to maintain approximately the same pH as in Example 2.

EXAMPLE 13

Dental whitening compositions within the scope of the present invention are made according to Example 12, except that all or part of the CARBOPOL 974 NF is replaced by at least one of the following thickening agents: xanthan gum, Irish moss gun, ghatti gum, furcelleran gum, carrageenan gum, arabic gum, alginic acid gum, agar gum, alginate gum, a tackifying protein, or a cellulosic ether.

EXAMPLE 14

A dental whitening composition within the scope of the present invention is made according to Example 1, except that the ingredients are combined in the following concentrations by weight percent:

| | |
|---|---|
| Glycerin | 89% |
| $KNO_3$ | 1% |
| Carbamide peroxide | 15% |

The foregoing procedure results in a dental whitening composition having similar opacifying and desensitizing capabilities compared to the composition of Example 2. However, the composition is less sticky than the composition of Example 2 and has greater bleaching capability.

EXAMPLE 15

To any of the foregoing dental whitening compositions is added one or more of the following antimicrobial agents for treatment of a patient's gums: chlorohexidine, tetracycline, cetyl pyridinium chloride, benzalkonium chloride, cetyl pyridinium bromide, methyl benzoate, and propyl benzoate. These compositions are preferably used in conjunction with a thin walled, flexible dental tray that overlaps the person's gums in order for the dental whitening compositions to contact the gums being treated.

EXAMPLE 16

To any of the foregoing dental whitening compositions which include a bleaching agent and do not include a bleaching agent stabilizer, one of the following chelating agents may be added: EDTA, monosodium EDTA, citric acid, succinic acid, and adipic acid.

From the foregoing, it will be appreciated that the present invention provides compositions and methods for whitening teeth.

The present invention also provides compositions for whitening teeth which reduce tooth sensitivity compared to conventional dental bleaching compositions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of bleaching a person's teeth and reducing tooth sensitivity, comprising:
providing a dental bleaching and desensitizing composition comprised of:
a peroxide dental bleaching agent included in an amount so as to have a tooth whitening effect when used to bleach teeth;
potassium nitrate in an amount so as to at least partially offset tooth sensitivity caused by the peroxide dental bleaching agent, wherein the potassium nitrate is included in a range of 0.01% to 2% by weight of the dental bleaching and desensitizing composition;
a fluoride salt in an amount so as to at least partially offset tooth sensitivity caused by the peroxide dental bleaching agent;
about 1% to about 50% by weight of water; and
a tackifying agent; and
contacting a person's teeth with the dental bleaching and desensitizing composition for at least about 15 minutes and so that the peroxide dental bleaching agent has a whitening effect on the person's teeth.

2. A method as recited in claim 1, wherein the peroxide dental bleaching agent is included in a range of about 0.5% to about 50% by weight of the dental bleaching and desensitizing composition.

3. A method as recited in claim 1, wherein the peroxide dental bleaching agent is included in a range of about 1% to about 30% by weight of the dental bleaching and desensitizing composition.

4. A method as recited in claim 1, wherein the peroxide dental bleaching agent is included in a range of about 3% to about 20% by weight of the dental bleaching and desensitizing composition.

5. A method as recited in claim 1, wherein the peroxide dental bleaching agent comprises at least one of hydrogen peroxide, carbamide peroxide, sodium perborate, benzoyl peroxide, or glycerol peroxide.

6. A method as recited in claim 1, wherein the potassium nitrate is included in a range of about 0.05% to about 1% by weight of the dental bleaching and desensitizing composition.

7. A method as recited in claim 1, wherein the potassium nitrate is included in an amount of 0.5% by weight of the dental bleaching and desensitizing composition.

8. A method as recited in claim 1, wherein the fluoride salt is included in an amount so as to provide from about 0.1% to about 1% fluoride by weight of the dental bleaching and desensitizing composition.

9. A method as recited in claim 1, wherein the fluoride salt is included in an amount so as to provide fluoride in a range of about 0.1% to about 0.5% by weight of the dental bleaching and desensitizing composition.

10. A method as recited in claim 1, wherein the fluoride salt is at least one of sodium monofluorophosphate, sodium fluoride, or stannous fluoride.

11. A method as recited in claim 1, further comprising a polyol.

12. A method as recited in claim 1, wherein the dental bleaching and desensitizing composition is contacted with the person's teeth using a dental tray.

13. A method of bleaching a person's teeth and reducing tooth sensitivity, comprising:
providing a dental bleaching and desensitizing composition comprised of:
a peroxide dental bleaching agent included in an amount so as to have a tooth whitening effect when used to bleach teeth;
potassium nitrate in a range of 0.01% to 2% by weight of the dental bleaching and desensitizing composition so as to at least partially offset tooth sensitivity caused by the peroxide dental bleaching agent;
fluoride in a range of about 0.1% to about 1% by weight of the dental bleaching and desensitizing composition so as to at least partially offset tooth sensitivity caused by the peroxide dental bleaching agent; and
a carrier; and
contacting a person's teeth with the dental bleaching and desensitizing composition for at least about 15 minutes and so that the peroxide dental bleaching agent has a whitening effect on the person's teeth.

14. A method as recited in claim 13, wherein the carrier comprises a tackifying agent and a polyol.

15. A method as recited in claim 14, wherein the dental bleaching and desensitizing composition is contacted with the person's teeth using a dental tray.

16. A method of bleaching a person's teeth and reducing tooth sensitivity, comprising:
providing a dental bleaching and desensitizing composition comprised of:
a peroxide dental bleaching agent included in an amount so as to have a tooth whitening effect when used to bleach teeth;
potassium nitrate in an amount in a range of 0.01% to 2% by weight of the dental bleaching and desensitizing composition so as to at least partially offset tooth sensitivity caused by the peroxide dental bleaching agent;
a fluoride salt in an amount so as to at least partially offset tooth sensitivity caused by the peroxide dental bleaching agent;
water;
a tackifying agent; and
a polyol;
introducing a quantity of the dental bleaching and desensitizing composition into a dental tray; and
placing the dental tray over a person's teeth for at least about 15 minutes in order for the dental bleaching and desensitizing composition to contact and have a whitening effect on the person's teeth.

17. A method as recited in claim 16, the potassium nitrate being included in a range of about 0.05% to about 1% by weight of the dental bleaching and desensitizing composition.

18. A method as recited in claim 16, the fluoride salt providing from about 0.1% to about 1% fluoride by weight of the dental bleaching and desensitizing composition.

19. A method as recited in claim 13, wherein the potassium nitrate is included in a range of about 0.05% to about 1% by weight of the dental bleaching and desensitizing composition.

20. A method as recited in claim 1, wherein the tackifying agent is included in a range of about 3% to about 25% by weight of the dental bleaching and desensitizing composition.

21. A method as recited in claim 16, wherein the water is included in a range of about 2% to about 50% by weight of the dental bleaching and desensitizing composition.

* * * * *